US009890376B2

(12) United States Patent
Gagnon

(10) Patent No.: US 9,890,376 B2
(45) Date of Patent: Feb. 13, 2018

(54) CHROMATOGRAPHIC PURIFICATION OF POLYNUCLEOTIDES WITH NEGATIVELY CHARGED PARTICLES

(71) Applicant: AGENCY FOR SCIENCE, TECHNOLOGY AND RESEARCH, Connexis (SG)

(72) Inventor: Peter Gagnon, Centros (SG)

(73) Assignee: AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 477 days.

(21) Appl. No.: 14/555,257

(22) Filed: Nov. 26, 2014

(65) Prior Publication Data
US 2015/0148528 A1 May 28, 2015

Related U.S. Application Data

(63) Continuation of application No. PCT/SG2013/000217, filed on May 30, 2013.

(60) Provisional application No. 61/653,694, filed on May 31, 2012, provisional application No. 61/773,666, filed on Mar. 6, 2013.

(51) Int. Cl.
| | |
|---|---|
| *C07H 21/00* | (2006.01) |
| *C12N 15/10* | (2006.01) |
| *B01D 15/36* | (2006.01) |
| *C07H 21/04* | (2006.01) |

(52) U.S. Cl.
CPC ......... *C12N 15/101* (2013.01); *B01D 15/362* (2013.01); *C07H 21/04* (2013.01); *C12N 15/1006* (2013.01); *C12N 15/1017* (2013.01)

(58) Field of Classification Search
CPC .................................................. C12N 15/101
USPC ...................................................... 536/25.4
See application file for complete search history.

(56) References Cited

U.S. PATENT DOCUMENTS

| | | | |
|---|---|---|---|
| 2004/0018559 A1 | 1/2004 | Lau et al. | |
| 2011/0319506 A1* | 12/2011 | Erbacher | C12N 15/1006 521/38 |

FOREIGN PATENT DOCUMENTS

| | | | |
|---|---|---|---|
| JP | 2005-533646 A1 | 11/2015 | |
| WO | WO 204/011141 A1 | 2/2004 | |
| WO | 2010027696 A1 | 11/2010 | |
| WO | 2012149200 A1 | 11/2012 | |

OTHER PUBLICATIONS

Cutler Methods in Molecular Biology,1996 vol. 59 Protein Purification Protocols Edited by S Doonan Humana Press Inc , Totowa, NJ.*
Supplementary European Search Report dated Nov. 27, 2015 in corresponding European Patent Application No. 13797414.3 (10 pages).
Urthaler, J. et al., "Industrial Scale cGMP Purification of Pharmaceutical Grade Plasmid-DNA", Chemical Engineering & Technology, Nov. 7, 2005, vol. 28, No. 11, pp. 1408-1420.
Gustavsson, P. et al. "Purification of plasmid DNA with a new type of anion-exchange beads having a non-charged surface", Journal of Chromatography, Elsevier Science Publishers B.V, NL, Jun. 4, 2004, vol. 1038, No. 1-2, pp. 131-140.
Kepka et al., "Integrated process for purification of plasmid DNA using aqueous two-phase systems combined with membrane filtration and lid bead chromatography", Journal of Chromatography, Elsevier Science Publishers B.V, NL, Nov. 19, 2004, vol. 1057, No. 1-2, pp. 115-124.
Ferreira, G. N. M., "Chromatographic Approaches in the Purification of Plasmid DNA for Therapy and Vaccination", Chemical Engineering and Technology, DE, Nov. 1, 2005, vol. 28, No. 11, pp. 1285-1294.
Nian et al., "Void exclusion of antibodies by grafted-ligand porous particle anion exchangers," J. Chromatogr. A 1282 (2013) 127-132.
Gagnon, "The Emerging Generation of Chromatography Tools for Virus Purification," BioProcess International Oct. 2008,8 pages.
Schmidt et al., "Investigation of particle-based and monolithic columns for cation exchange protein displacement chromatography using poly(diallyl-dimethylammonium chloride) as displacer," Journal of Chromatography A, 1018.
Hunter et al., "Protein adsorption on novel acrylamido-based polymeric ion-exchangers I. Morphology and equilibrium adsorption, " Journal of Chromatography A, 897 (2000) 65-80.
Hunter et al., "Protein adsorption on novel acrylamido-based polymeric ion exchangers II. Adsorption rates and column behavior, " Journal of Chromatography A, 897 (2000) 81-97.
Hunter et al., "Protein adsorption on novel acrylamido-based polymeric ion-exchangers III. Salt concentration effects and elution behavior," Journal of Chromatography A, 930 (2001) 79-93.
Hunter et al., "Protein adsorption on novel acrylamido-based polymeric ion-exchangers IV. Effects of protein size on adsorption capacity and rat," Journal of Chromatography A, 971 (2002) 105-116.
Japanese Office Action dated Dec. 6, 2016 for Appln. No. 2015-514966.

* cited by examiner

Primary Examiner — Jezia Riley
(74) Attorney, Agent, or Firm — Pillsbury, Winthrop Shaw Pittman LLP

(57) ABSTRACT

A method of purifying a sample that includes a polynucleotide includes the steps of (i) providing a packed chromatographic column having negatively charged porous particles, (ii) equilibrating the column to the conditions to which the polynucleotide in the sample is to elute, (iii) contacting the sample with the packed chromatographic column such that the sample volume applied to the packed chromatographic column is less than or equal to the interparticle space of the negatively charged porous particles within the packed chromatographic column, (iv) eluting the polynucleotide from the packed chromatographic column, where the polynucleotide is in a purer state and in the conditions to which the packed chromatographic column was equilibrated.

29 Claims, No Drawings

CHROMATOGRAPHIC PURIFICATION OF POLYNUCLEOTIDES WITH NEGATIVELY CHARGED PARTICLES

CROSS-REFERENCE TO RELATED APPLICATIONS

This application is a continuation of PCT/SG2013/000217 filed May 30, 2013, which claims the priority of U.S. Provisional Application No. 61/653,694, filed May 31, 2012 and U.S. Provisional Application No. 61/773,666 filed Mar. 6, 2013, the disclosures of which are incorporated herein by reference in their entireties.

FIELD OF THE INVENTION

This invention relates to methods for the purification of polynucleotides. It further relates to the integration of these capabilities with other purification methods to achieve the desired level of final purification.

BACKGROUND OF THE INVENTION

Solid materials with charged surfaces are used widely in the field of polynucleotide purification. These materials commonly include ion exchangers, which are usually employed in either of two application formats. In bind-elute mode, the polynucleotide and ion exchanger are equilibrated to conditions that allow the polynucleotide species of interest to bind. Contaminants that interact weakly or not at all with the charged surface fail to bind and are eliminated. Contaminants that interact more strongly than the polynucleotide bind more strongly. After washing to remove unbound contaminants, the column may be eluted by increasing the salt concentration. This permits fractionation of bound species in increasing order of the strength of their interaction with the ion exchanger, thereby achieving a high degree of polynucleotide purification. In flow-through mode, for example on a cation exchanger, the sample and ion exchanger are both equilibrated to conditions that prevent the polynucleotide from binding. Species that interact more strongly with the ion exchanger than the polynucleotide are bound and thereby removed, but species that bind more weakly than the polynucleotide flow through with it and persist as contaminants. Both modes are performed on charged surfaces presented in a variety of solid phase architectures, including porous or non-porous particles packed in columns, or added directly to large volume aqueous samples, or on monoliths or membranes. These different architectures confer different flow properties, capacity, and resolution, but the defining chemical features of flow-through or bind-elute chromatography are constant regardless of physical format. Both methods rely on the equilibration of the ion exchanger and sample to the same conditions before the sample is introduced to the column.

Some chromatography media embody combinations of charges with other types of chemical functionalities. These media are broadly known as mixed-modes or multimodal materials, and may variously combine charges with hydrophobic groups, metal affinity, groups, or chemical groups that favor formation of hydrogen bonds. They are operated under different chemical conditions depending on the nature of the secondary functionalities, but they are still operated in bind-elute and flow-through mode.

A small minority of multimodal materials have been described that combine charge with a physical functionality, for example, where a charged material also has the ability to sort species according to their size. One such example employs variable size exclusion functionality in combination with an electropositive surface [Hunter, A., J. Chromatogr. A 897:65-80 (2000); Hunter, A., J. Chromatogr. A 897:81-97 (2000); Hunter, A., J. Chromatogr. A 930:79-93 (2000); Hunter, A., J. Chromatogr. A 971:105-116 (2000)]. The method generally involves entry of proteins into particle pores in a size-dependent manner while exhibiting codependence on the charge on the protein, as well as the buffer conditions. Like other charged materials for fractionation, the method employs bind-elute and flow-through modes of operation.

Recently (Nian et al. J. Chromatogr. A 1282 (2013) 127-132.) a new mode of chromatography has been described called void exclusion chromatography. The material for practicing the method includes a column packed with electropositive particles (cf. Hunter supra), with the proviso that the sample volume applied to a column is not greater than the volume occupied by the space between the particles. The method was described for purification of antibodies.

SUMMARY OF THE INVENTION

Methods, materials, and kits are provided for the purification of polynucleotide. In certain embodiments, the invention provides methods for purifying a sample comprising polynucleotide including the steps of (i) providing a packed chromatographic column comprising negatively charged porous particles, (ii) equilibrating the packed chromatographic column to the conditions to allow the polynucleotide in the sample to elute, (iii) contacting the sample with the packed chromatographic column such that the sample volume applied to the packed chromatographic column is less than or equal to the interparticle space of the negatively charged porous particles within the packed chromatographic column, and (iv) eluting the polynucleotide from the packed chromatographic column, wherein the polynucleotide is in a purer state.

DETAILED DESCRIPTION OF THE INVENTION

In certain embodiments, the present invention relates to a column packed with electronegative porous particles in which polynucleotide may be substantially restricted to the space between particles (i.e. the inter-particle or void space) by the force of electrostatic repulsion, independently from or in combination with steric rejection from the pores, or solely by steric rejection from the pores. This may cause the polynucleotide to transit the column substantially if not exclusively through the void space. Steric rejection, in particular, refers to a mechanism whereby polynucleotide is unable to enter the pore space under conditions which prevent it from overcoming physical resistance exerted by the configuration of negatively charged ligands within the pores. Many of the contaminating proteins (including those arising from the host cell from which the polynucleotide was produced) and cell culture media components, including salts, nonionic, and zwitterionic species are able to enter the pores of the particles, which is believed, without being bound to any specific theory, to retard their transport through the column and causes them to become separated from the faster-migrating polynucleotide as buffer flows through the column. Acidic contaminants may be further retarded by binding to the electronegative surface.

It has been discovered that this method permits effective fractionation of, inter alia, polynucleotide without respect to the sample conditions, without respect to the chemical characteristics of most contaminants, and without respect to the composition of the buffer that is applied immediately following sample application to impel the polynucleotide through the column. In certain embodiments, it is an advantage of the invention that it may be practiced at a wide range of conditions (pH, salt concentration, conductivity, etc.) and therefore those conditions may be selected for convenient performance of the methods of the invention in conjunction with processes preceding or following the methods of the invention in the course of the manufacture and purification of polynucleotide. In certain embodiments, these unique operating features and results may be achieved by limiting sample application to a volume not exceeding the inter-particle volume of the negatively charged particles within the column. Additionally, in some embodiments, the method is neither applied with other types of negatively charged materials, including non-porous particles, membranes, or monoliths, nor is it applied by dispersing negatively charged porous or non-porous particles or soluble negatively charged polymers within a sample. Rather, in some embodiments of the invention, the method is performed with a packed column of porous particles. In certain embodiments, the invention is highly advantageous over other method of polynucleotide purification using columns packed with porous particles because transport through the interparticle space is convective, rather than diffusive. This allows the method to be carried out effectively at higher flow rates than other particle-column methods, which translates into higher productivity.

It has been further discovered that the innate fractionation ability of certain embodiments of the invention may be enhanced by including additional surface functionalities on particles within the column bed, so long as the column is equilibrated to conditions that do not cause the polynucleotide to be retained or significantly retarded by those additional functionalities. Such functionalities may include but are not restricted to positively charged groups, hydrophobic groups, pi-pi bonding groups, hydrogen-bonding groups, or metal-chelation groups. These additional functionalities may reside on the same chemical moiety as the negatively charged groups, on the same porous particles as the negatively charged groups, or on different particles that may be porous or non-porous. In the event that secondary functionalities are added through inclusion of additional particles, the volume of sample that may be applied may be limited to a volume corresponding to the inter-particle space that would exist between only the negatively charged porous particles in the column. This volume can be estimated at about 40% of the gravity-settled volume of negatively charged porous particles in a column, but may be less if the particle bed is physically compressed, and can be determined quantitatively by experimentation.

In certain embodiments, the degree of purification afforded by the method can be enhanced by pre-treating the sample with agents to promote dissociation of contaminants that may have come to be associated with the polynucleotide. Such agents particularly include various dissociating agents, including elevated concentrations of salts, urea, amino acids, nonionic organic polymers, organic solvents, and surfactants, among others. In certain embodiments, the chaotropic salt guanidine at concentrations up to 6 M may be particularly useful for dissociating polynucleotide from freshly homogenized cells or other complex preparations. The dissociating agents are removed with other small molecules in the sample, during routine practice of the method. This highlights two advantages of the invention, the first is that it requires no previous equilibration of sample to the conditions under which the column will be run, even when the sample conditions are radically unsuitable for conducting ion exchange chromatography in bind-elute or flow-through mode, and the second is that the sample elutes in the buffer used to equilibrate the column, no matter what the composition of the sample, thus achieving buffer exchange in conjunction with purification of the polynucleotide.

In certain embodiments, the invention provides methods for purifying a sample containing polynucleotide including the steps of (i) providing a packed chromatographic column comprising negatively charged porous particles, (ii) equilibrating the column to the conditions to which the polynucleotide in the sample is to elute, (iii) contacting the sample with the column such that the sample volume applied to the column is less than or equal to the interparticle space of the negatively charged porous particles within the column, (iv) eluting the polynucleotide from the column, wherein the polynucleotide is in a purer state and in the conditions to which the column was equilibrated.

In the preceding embodiment, the polynucleotide species may be genomic polynucleotide, a polynucleotide fragment, or a polynucleotide plasmid. The polynucleotide may be of natural or recombinant origin.

In one or more of each of the preceding embodiments, the sample may be previously unpurified.

In one or more of each of the preceding embodiments, the sample may be concentrated prior to practicing the invention.

In one or more of each of the preceding embodiments, the sample may have been concentrated by ultrafiltration.

In one or more of each of the preceding embodiments, the sample may have undergone a previous purifying step to an intermediate level or high level of purity.

In one or more of each of the preceding embodiments, the intermediate level of purity of the sample may be in a range from about 40% to about 90% purity, or greater.

In one or more of each of the preceding embodiments, the high level of purity of the sample may be about 90% or greater.

In one or more of each of the preceding embodiments, the sample volume may be less than 90% of the interparticle space of the negatively charged porous particles within the packed chromatographic column.

In one or more of each of the preceding embodiments, the sample volume may be less than 80% of the interparticle space of the negatively charged porous particles within the packed chromatographic column.

In one or more of each of the preceding embodiments, the sample volume may be less than 70% of the interparticle space of the negatively charged porous particles within the packed chromatographic column.

In one or more of each of the preceding embodiments, the sample volume may be less than 60% of the interparticle space of the negatively charged porous particles within the packed chromatographic column.

In one or more of each of the preceding embodiments, the sample volume may be less than 50% of the interparticle space of the negatively charged porous particles within the packed chromatographic column.

In one or more of each of the preceding embodiments, the sample volume may be less than 0.1% of the interparticle space of the negatively charged porous particles within the packed chromatographic column.

In one or more of each of the preceding embodiments, the packed chromatographic column may be packed solely with negatively charged porous particles and the sample volume may be less than 40% of the volume of the packed chromatographic column.

In one or more of each of the preceding embodiments, a sample application condition comprises a pH in a range of from approximately 2 to a pH of approximately 9.

In one or more of each of the preceding embodiments, the packed chromatographic column may be equilibrated to a pH between approximately 4 and approximately 8.

In one or more of each of the preceding embodiments, the packed chromatographic column may be equilibrated with a buffer at a pH between about 4.5 and about 6.0.

In one or more of each of the preceding embodiments, a sample application condition comprises a conductivity value in range of from approximately 0.1 mS/cm to approximately 250 mS/cm.

In one or more of each of the preceding embodiments, the packed chromatographic column may be equilibrated to a conductivity value of from approximately 0.1 mS/cm to approximately 30 mS/cm.

In one or more of each of the preceding embodiments, the packed chromatographic column may be equilibrated to a conductivity value of from about 0.1 to about 15 mS/cm.

In one or more of each of the preceding embodiments, the packed chromatographic column may be equilibrated with a buffer at a pH of about 4.5 and a non-zero conductivity value less than about 1 mS/cm.

In one or more of each of the preceding embodiments, the packed chromatographic column may be equilibrated to conditions at or close to a sample application condition for a subsequent purification step to be performed upon the eluate.

In one or more of each of the preceding embodiments, the negatively charged porous particles are cation exchange particles.

In one or more of each of the preceding embodiments, the cation exchange particles possess an electronegativity, at least of portion of the electronegativity being provided by a moiety selected from the group consisting of carboxyl groups, sulfo groups, or phosphoryl groups.

In one or more of each of the preceding embodiments, electronegativity may be conferred by more than one species of negatively charged moiety.

In one or more of each of the preceding embodiments, electronegativity may be conferred by complex ligands that include carboxyl, sulfo, or phospho groups in combination with other functionalities that confer secondary reactivities. In one such embodiment, electronegativity may be conferred by a complex ligand that includes one or more carboxyls in combination with at least one amino group such that the negatively charged ligand embodies a strong ability to participate in metal coordination. An example of such a ligand could be iminodiacetic acid, or nitriloacetic acid. In another such embodiment, the complex ligand may comprise an aromatic or aliphatic hydrophobic group covalently linked directly or indirectly to one or more negative charges.

In one or more of each of the preceding embodiments, the packed chromatographic column further comprises other particles in addition to the electronegative porous particles.

In one or more of each of the preceding embodiments, at least one of the electronegative porous particles or the other particles comprise one or more secondary chemical functionalities selected from the group consisting of anion exchange, hydrophobic interactions, hydrogen bonding, pi-pi interactions, and metal chelation.

In one or more of each of the preceding embodiments, the method may further comprise the additional step of contacting the sample with one or more species of dissociating agents prior to the step of contacting the sample with the packed chromatographic column, where the purpose of the dissociating agent is to dissociate the polynucleotide species from contaminants with which it may be associated non-specifically.

In one or more of each of the preceding embodiments, the dissociation agent may be an organic solvent.

In one or more of each of the preceding embodiments, the dissociating agent may be ethylene glycol, propylene glycol, polyethylene glycol, dimethyl sulfoxide, glycerol, ethanol, or isopropanol.

In one or more of the preceding embodiments, the dissociating agent may be present at a concentration ranging from a non-zero amount, to 0.1% or more, 1% or more, 10% or more, or 20% or more.

In one or more of the preceding embodiments, the dissociating agent may be a chaotrope, such as urea, from a non-zero concentration to 8 M or more, for example 0.5 M or more, 1 M or more, 2 M or more, 4 M or more, 6 M or more.

In one or more of the preceding embodiments, the dissociating agent may be a surfactant.

In one or more of the preceding embodiments, the surfactant may be a nonionic such as Triton or Tween or Brij; or a zwitterionic surfactant such as CHAPS, CHAPSO, or octaglucoside.

In one or more of the preceding embodiments, the surfactant may be present in the sample at a concentration of less than 0.1%.

In one or more of the preceding embodiments, the dissociating agent may be a hydrogen bond disruptor, such as urea or sorbitol.

In one or more of the preceding embodiments, the dissociating agent may be an amino acid, such as arginine, lysine, or histidine.

In one or more of the preceding embodiments, the amino acid may be at a concentration ranging from a non-zero amount to 500 mM.

In one or more of the preceding embodiments, the dissociating agent may be a chelating agent, such as ethylene diamine tetraacetic acid (EDTA), tris(2-aminoethyl)amine (TREN), or deferoxamine.

In one or more of the preceding embodiments, the chelating agent may be at a concentration ranging from a non-zero amount to 50 mM.

In one or more of each of the preceding embodiments, the method may further comprise the additional step of contacting the sample with one or more species of salt prior to the step of contacting the sample with the packed chromatographic column, where the purpose of the salt is to dissociate the polynucleotide species from contaminants with which it may be associated non-specifically.

In one or more of the preceding embodiments, the salt added to the sample may consist of sodium chloride, potassium chloride, or other so-called neutral salt.

In one or more of the preceding embodiments, the salt added to the sample may consist of a chaotropic salt, such as guanidine.

In one or more of the preceding embodiments, the salt may be at a concentration ranging from a non-zero amount to 2 M or more; for example 50 mM or more, 100 mM or more, 200 mM or more, 500 mM or more, 1 M or more.

In one or more of each of the preceding embodiments, the contaminant may be a metal ion, protein, lipid, endotoxin, virus, cell culture media component, an undesired species of nucleotide, or combinations thereof.

In one or more of each of the preceding embodiments, the sample may contain one or more contaminants wherein the purer state of the polynucleotide has a reduced content of such contaminants in comparison with the sample as a result of performing the methods disclosed herein.

A kit may be provided for the convenient practice of a method according to any of the preceding embodiments.

In certain embodiments, the inter-particle space is greater than approximately twice the volume of the sample. In certain embodiments, the inter-particle space of the portion of the column containing porous electronegative particles is greater than the sample volume. In certain embodiments, having columns packed solely with negatively charged porous particles the sample volume is about 40% or less than the volume of the packed column; in certain embodiments having columns packed with negatively charged porous particles and other particles, the sample volume is about 40% or less than the volume of the gravity settled negatively charged porous particles in the column.

In certain embodiments, the interparticle space of the negatively charged porous particles packed in the columns is approximately the same volume as the sample, or 10% greater than the sample volume, or 20, 30, 40, 50, 60, 70, 80, 90, or 100% greater than the sample, or 1.5 or 2 or 2.5 or 3 or 4 or 5 or more times greater than the sample.

In certain embodiments, the column is equilibrated with an equilibration buffer prior to contacting the sample with the column. In certain such embodiments, the column is equilibrated to a pH between approximately 3 and approximately 9. In certain such embodiments, the column is equilibrated with a buffer at a pH between about 4 and about 6.0. In certain such embodiments, the column is equilibrated with a buffer at a pH between about 4.5 and about 5.5. In certain embodiments, the column is equilibrated to a conductivity value of from approximately 1 mS/cm and approximately 30 mS/cm. In certain embodiments, the pH, salt concentration and conductivity conditions for the column are selected such that electrostatic interactions between the electronegative porous particles and components from the sample other than the polynucleotide are substantially suspended. The pH, salt concentration and conductivity conditions for the equilibration buffer and or the elution buffer may be chosen in certain embodiments of the invention such that electrostatic interactions between the electronegative porous particles and components from the sample other than the desired protein are substantially suspended. In certain embodiments, the conductivity of the equilibrated column is between about 0.1 and about 15 mS/cm. In certain embodiments, the column may be equilibrated to conditions at or close to the sample application conditions for a subsequent purification step to be performed upon the eluate.

In certain embodiments, the sample conditions may range from pH of approximately 3 to a pH of approximately 10. In certain such embodiments, the conductivity values of the sample may range from approximately 0.1 mS/cm to approximately 250 mS/cm. In certain embodiments, the sample conditions may range from pH of approximately 2 to a pH of approximately 10 and in certain embodiments, the conductivity values of the sample conditions may range from approximately 0.1 mS/cm to approximately 250 mS/cm.

In certain embodiments, the elution conditions may range from a pH of approximately 2 to a pH of approximately 10. In certain such embodiments, the conductivity of the buffer applied immediately after the sample may range from approximately 0.1 mS/cm to approximately 250 mS/cm. In certain embodiments, the buffer applied immediately after the sample has lower conductivity than the sample or equilibration buffer. In certain embodiments, the buffer applied immediately after the sample has higher conductivity than the sample or equilibration buffer.

In certain embodiments, the column equilibration buffer may be of a pH of about 5.0 and a conductivity of less than 1 mS/cm, such as mediated by a 20 mM or lower concentration of acetic acid without added salt. In some embodiments, the concentration of acetate may be in a range of from about 20 mM to about 50 mM.

In certain embodiments, the buffer applied immediately after the sample may have the same composition as the equilibration buffer. In certain embodiments, the buffer applied after the sample may have a different composition from the equilibration buffer. In certain embodiments, the buffer applied immediately after the sample may be of much higher conductivity than the equilibration buffer, with the object of removing positively charged materials that may be bound to the negatively charged particles.

In certain embodiments, excess salt or other additives may be included in the sample to clean the column in preparation for a subsequent usage cycle. It will be understood that such additives may also mediate the beneficial effect of dissociating non-specific interactions between the polynucleotide and contaminant species, with the result of increasing the degree of purity and or aggregate reduction achieved by the technique.

In certain embodiments, the negatively charged porous particles are cation exchange particles. In certain such embodiments, the cation exchange particles possess an electronegativity which is conferred in part by a moiety such as a carboxyl group, a sulfo group, a phospho group, an iminodiacetic acid group, or a nitriloacetic acid group. In certain embodiments, the column contains particles in addition to the electronegative porous particles. In certain embodiments, at least one of the electronegative porous particles and the additional particles possess one or more secondary chemical functionalities selected from the group consisting of cation exchange, hydrophobic interactions, hydrogen bonding, pi-pi interactions, and metal chelation.

In certain embodiments, the technique makes use of so-called grafted-ligands that create a dense network of charged groups within the pores of the particles, such that the network physically hinders or prevents the entry of solutes that lack a strong positive charge.

In certain embodiments, the technique makes use of negatively charged porous particle chromatography media having a pore size that prevents effective entry of polynucleotide. Exemplary pore sizes useful in preventing entry of polynucleotide particles include a range of from about 10 nm to about 100 nm, including any values in between and fractions thereof, depending on the size of the polynucleotide. One skilled in the art will appreciate that pore sizes less than 10 nm may also be employed including, without limitation, 1, 2, 3, 4, 5, 6, 7, 8, or 9 nm. Likewise, one skilled in the art will also appreciate that pore sizes greater than 100 nm may be employed including, without limitation, 120, 150, 200, 300, and 500 nm, including any values in between and fractions thereof. Those skilled in the art will recognize an appropriate selection of pore size based on the polynucleotide to be purified. Such porous particles may constitute the entire sample volume, or any smaller proportion thereof.

In certain embodiments, the invention provides for the additional step of contacting the sample with a dissociating agent prior to the step of contacting the sample with the column. In certain such embodiments, a dissociating agent may be a salt, an organic solvent, or an organic polymer, a hydrogen bond disruptor, a chaotrope, a surfactant, or a chelating agent.

In certain embodiments, the invention provides for the additional step of contacting the sample with more than one dissociating agent prior to the step of contacting the sample with the column. In certain such embodiments, the dissociating agents may be include more than one of any of the following classes of dissociating agent, or combination of agents from different classes, where the classes include, for example: a salt, an organic solvent, or an organic polymer, a hydrogen bond disruptor, a chaotrope, a surfactant, or a chelating agent.

In certain such embodiments, the dissociating agent is a nonionic organic polymer selected from the group consisting of polyethylene glycol, polypropylene glycol and polybutylene glycol. In certain such embodiments, the dissociating agent has an average molecular weight of approximately 500 D or less. In certain such embodiments, the dissociating agent is an organic solvent selected from the group consisting of ethylene glycol, propylene glycol, butylene glycol, dimethylsulfoxide, ethanol, and glycerol. In certain such embodiments, the dissociating agent is provided at a concentration of approximately 1% (w/v) or greater.

In certain embodiments, the dissociating agent is a surfactant selected from the group consisting of Tween, triton, CHAPS, CHAPSO and octyl glucoside. In certain such embodiments, the surfactant is provided at a non-zero concentration of approximately 1% (w/v) or less, or at a non-zero concentration of approximately 0.1% (w/v) or less.

In certain embodiments, the invention provides methods including the additional step of removing insoluble solids prior to the step of contacting the sample with the column.

In certain embodiments, the invention provides methods in which the sample contains one or more contaminants wherein the purer state of the polynucleotide resulting from performance of the method has a reduced content of such contaminants in comparison with the sample. For example, in some embodiments, where the contaminant is a protein, the protein concentration may be reduced by more than 10-fold, or more than 20-fold, or more than 50-fold, or more than 90-fold, or more than 95-fold.

In certain embodiments, a clarified but still otherwise unpurified sample is conditioned by exposure to negatively charged particles under conditions where the polynucleotide is substantially unbound by those particles, for the purpose of scavenging highly acidic contaminants before practicing the invention. In one such embodiment the negatively charged particles are added directly to the sample, for example in an amount of about 2-5% (v:v) of the entire sample volume. In certain such embodiments the negatively charged particles include secondary functionalities such as the ability to participate in hydrophobic interactions or metal coordination. In such embodiments, this practice will be understood to improve the performance of the invention by removing sample components that could interfere with the interaction of the polynucleotide with the negatively charged column-packed particles used to practice the invention. In certain such embodiments, this treatment takes place prior to concentration of the polynucleotide by ultrafiltration. In other such embodiments this treatment may take place without an associated ultrafiltration step. In other such embodiments, this treatment takes place after concentration of the polynucleotide by ultrafiltration. In the first case, it will be understood to potentially improve the performance of the ultrafiltration step. In the last case it will be understood to reduce the volume of the treatment process and the volume of negatively charged particles required to scavenge highly acidic contaminants. In any case, an intermediate step may be added prior to remove the particles prior to treatment by the invention.

In certain embodiments, the invention provides a kit for the convenient practice of a method of the invention including some or all of the materials needed for performance of the invention, preferably in amounts and concentrations convenient for the performance of a method of the invention. Such kits may also include instructions for use of the materials provided in the kit.

The following terms are defined so that the invention may be understood more readily. Additional definitions are set forth throughout the detailed description.

"Column equilibration" refers to achieving a stable and equal distribution of a desired buffer in a column packed with a chromatography medium. At equilibrium, the pH, conductivity and UV absorption of eluent measured at a column outlet, are substantially identical to the eluent being introduced at the column inlet.

"Column volume" refers to the total volume of packed particles within a usually cylindrical device called a column. The term column volume is generally understood to correspond to the so-called total column volume, which is comprised of three parts, those being the interparticle space known as the void volume, the volume within the pores known as the pore volume, and the volume occupied by the solid matrix of the particle frequently referred to as the matrix volume.

"Conductivity value" refers to ability of an electrolyte solution to conduct electricity. The conductivity of a solution of an electrolyte can be measured by, for example, determining the resistance of the solution between two electrodes separated by a fixed distance. Conductivity values are most commonly expressed as milliSiemens per cm (mS/cm).

"Contaminant" refers to any undesired inorganic or organic entity that reduces the purity of a polynucleotide. Contaminants include entities that can form association with the polynucleotide that remain stable over a wide variety of conditions. Methods of the invention can provide for the active dissociation of such aggregates to recover the polynucleotide from a contaminant with which it is associated. Exemplary contaminants particularly include proteins, but also include polynucleotide, cell contents, cell culture media components and the like.

"Electronegative porous particle" or "negatively charged porous particle" refers to an insoluble solid that may be roughly spherical or not, and may have pores of any size. Optionally particles may be of a size ranging from less than 10 to more than 100 microns and the average pore size may range from less than 10 nm (microporous) to more than 100 nm (macroporous). Electronegativity of a particle may be conferred by chemical groups including but not limited to weak anion exchange groups, carboxyl or phosphor groups, strong anion exchange groups, such as sulfo groups, or multimodal moieties with a net negative charge, or combinations of the foregoing. Secondary functionalities that create a multimodal character on a negatively charged surface may consist of negatively or positively charged groups, hydrophobic groups, pi-pi bonding groups, hydrogen-bonding groups, or metal-chelation groups. The secondary functionalities may exist on electronegative particles as an inadvertent byproduct of the manufacturing materials or process by which the particles are synthesized, or they may be present by deliberate design. The concentration of secondary functionalities may range from less than 1 milliequivalent per mL of particles, to more than 100 milliequivalents per mL. The term electronegative porous particle includes commercial porous particle chromatography materials referred to as cation exchangers and may include so-called mixed mode chromatography materials that are electronegative.

"Inter-particle volume" or "void volume" refers to the volume within a column not occupied by the particles themselves; the space between the particles. This is frequently referred to as the void volume of a column. For roughly spherical particles of similar size, the void volume typically constitutes about 40% of a column packed with those particles when the particles are settled by gravity and not physically compressed by mechanical means.

"Pore volume" refers to the volume within the pores of porous particles. The pores maybe physically unobstructed, with positively charged groups distributed primarily on the pore walls, or partially obstructed with positively charged groups distributed on or within a network of polymers residing within the pores. Where the pores are partially obstructed, the degree of apparent obstruction may vary with the charge characteristics of the antibody or other sample components, and/or as a function of buffer conditions such as pH and conductivity.

"Non-ionic organic polymer" refers to a naturally occurring or synthetic hydrocarbon composed of linked repeating organic subunits that lack charged groups. It may be linear, dominantly linear with some branching, or dominantly branched. Examples suitable to practice the invention include but are not limited to polyethylene glycol (PEG), polypropylene glycol, and polyvinylpyrrolidone (PVP). PEG has a structural formula HO—$(CH_2—CH_2—O)_n$—H. Examples include, but are not limited to compositions with an average polymer molecular weight ranging from less than 100 to more than 1000 daltons.

"Dissociating agent" refers to an organic or inorganic compound that can reduce or, in conjunction with other reagents, aid in reducing contamination by promoting the dissociation of contaminants from the polynucleotide to be purified. Organic dissociating agents can include, without limitation, ureides, amino acids, nonionic organic polymers, organic solvents, chelating agents, and surfactants, among others. Inorganic dissociating agents particularly include salts.

"Organic solvent" refers to naturally occurring or synthetic organic compound existing in a liquid state. Examples suitable to practice the invention include but are not limited to ethylene glycol, propylene glycol, glycerol, dimethyl sulfoxide, ethanol, and phenoxyethanol.

"Polynucleotide" refers to a biopolymer composed of multiple nucleotide monomers covalently bonded in a chain. DNA (deoxyribonucleic acid) and RNA (ribonucleic acid) are examples of polynucleotides. Examples of polynucleotides include, without limitation, genomic DNA, cDNA, double-stranded DNA (dsDNA), single-stranded DNA (ssDNA), messenger RNA (mRNA), short interfering RNA (siRNA), microRNA (miRNA), and the like. Polynucleotides can have a high propensity for formation of hydrogen bonds. Such polynucleotides may occur in a range of sizes and configurations, any of which can be processed by the invention. Polynucleotides can be single strand, double strand, or triple strand.

Polynucleotides may also include unnatural polynucleotides, including those with an unnatural backbone, such as thiophosphate backbone, or those which incorporate unnatural bases. Polynucleotides may also include peptide nucleic acids (PNA).

"Protein" refers to any of a group of complex organic macromolecules that contain carbon, hydrogen, oxygen, nitrogen, and usually sulfur and are composed principally of one or more chains of amino acids linked by peptide bounds. The protein may be of natural or recombinant origin. Proteins may be modified with non-amino acid moieties such as through glycosylation, pegylation, or conjugation with other chemical moieties. Examples of proteins include but are not limited to antibodies, clotting factors, enzymes, and peptide hormones.

"Polynucleotide preparation" refers to any aqueous or mostly aqueous solution containing a polynucleotide of interest, such as a cell-containing cell culture harvest, a (substantially) cell-free cell culture supernatant, or a solution containing the polynucleotide of interest from a stage of purification.

"Sample application condition" refers to how the sample containing the desired protein is supplied and includes, for example, sample concentration, eluent conductivity, pH, and the like. The sample application condition may generally be selected to the conditions under which the column is equilibrated for the ensuing purification, or may differ from such conditions.

"Solid material" refers to an insoluble organic solid that may be particulate, crystalline, polymeric, fibrous, porous-hollow fibrous, monolithic, or membranaceous in nature. It may consist of non-porous or porous particles, a porous membrane, a porous filter, or a porous monolith. If particulate, the particles may be roughly spherical or not, and may be of sizes ranging from less than 100 nm to more than 100 microns. The average pore size of porous particles may range from less than about 10 nm (microporous) to more than about 100 nm (macroporous). The average pore size in membranes may range from less than 100 nm to more than 1 micron. The average channel size in membranes or monoliths may range from less than 1 micron to more than 10 microns. The solid material may further consist of compound constructions, for example in which particles are embedded in a reticular matrix, sandwiched between membranes, or both.

"Surfactant" includes "surface active agents" such as a class of organic molecules that generally embody a hydrophobic portion and a hydrophilic portion, causing them to be referred to as amphiphilic. At sufficient concentrations in aqueous solutions, surfactants can self-associate into clusters with the hydrophobic portions concentrated at the center to minimize contact with water, and the hydrophilic portions radiating outwards to maximize contract with water. In the presence of biological preparations, especially those containing materials that have a hydrophobic character or possess areas of hydrophobic character, the hydrophobic portion of surfactants tend to associate spontaneously with some portions of the hydrophobic material and increase their solubility through the influence of the hydrophilic portion of the surfactant. They may also be used to modulate hydrophobic interactions that occur between differing hydrophobic materials both dissolved in an aqueous solvent. Examples of surfactants suitable for practicing certain embodiments of the invention include but are not limited to nonionic surfactants such as polysorbate surfactants (e.g., Tween 20, Polyoxyethylene (20) sorbitan monolaurate, and Tween 80, Polyoxyethylene (20) sorbitan monooleate) and Triton (e.g., polyethylene glycol p-(1,1,3,3-tetramethylbutyl)-phenyl ether), and zwitterionic surfactants such as CHAPS (3-[(3-Cholamidopropyl)dimethylammoniol-1-propanesulfonate), CHAPSO (3-R3-cholamidopropyl) dimethylammonio]-2-hydroxy-1-propanesulfonate), and octyl glucoside (e.g., (2R,3S,4S,5R,6R)-2-(hydroxymethyl)-6-octoxyoxane-3,4,5-triol).

"Ureide" refers to a cyclic or acyclic organic molecule of natural or synthetic origin that comprises one or more urea moieties or derivatives thereof. In certain embodiments, the invention provides ureides such as urea, uric acid, hydantoin, allantoin (CAS number 97-59-6; alcloxa, aldioxa, hemocane, ureidohydantoin, 5-ureidohydantoin, glyoxylureide, glyoxylic acid diureide, 2,5-dioxo-4-imidazolidinyl urea), purines, and derivatives thereof. In certain embodiments, the invention provides organic molecules of the formula R—CO—NH—CO—NH$_2$ or R—CO—NH—CO—NH—CO—NH—CO—R' or R'R"NH—CO—NR'"R"" where the relevant "R-groups" may be H or any organic moiety.

"Void exclusion" refers to a chemical interaction by which at least one component of a sample inside the environment of a column packed with electrostatically charged particles is constrained to reside substantially within the interparticle space of the column bed as a result of being electrostatically repelled and/or unable to overcome physical resistance to pore entry that may be imposed either by the inherent dimension of the pores residing in the particles, or imposed secondarily by the physical format in which electrostatic charges are presented within the pores.

"Void exclusion mode" or "void exclusion chromatography" refers to a fractionation method practiced in columns of packed electrostatically charged particles, whereby the sample volume applied to the column is not greater than the interparticle volume within the packed bed, and a desired sample component, such as a protein, is unable to enter the pores of the particles, and is thereby constrained to travel through the interparticle space, which is also known commonly as the void volume. A fundamental and distinctive feature of void exclusion chromatography is that the sample need not be equilibrated to the column operating conditions, as a result of which the sample conditions may include extremely high salt concentrations and pH values considered unsuitable for conducting chromatography on electrostatically charged particles. Further fundamental and distinctive features includes its unique ability to achieve buffer exchange in conjunction with fractionation. In void exclusion chromatography, the desired protein elutes in the buffer to which the column is equilibrated, independent of the sample composition in which it was applied to the column.

In certain embodiments, polynucleotide can be eluted in the same buffer to which the column is equilibrated prior to sample application. In such embodiments the invention can provide an advantage that it can be used for the purpose of exchanging the buffer in which the sample resides, from its initial formulation to a formulation more suitable for subsequent processing by other methods. While the composition of buffer in which the sample initially resides is unrestricted except by the need to avoid damaging the polynucleotide, the composition of the column equilibration buffer must be within a range that does not create positive charge on the polynucleotide at a level sufficient to cause a substantial proportion of the polynucleotide to bind to the negatively charged particles. Appropriate equilibration conditions vary according to the choice of negatively charged porous particles and the particular features of specific polynucleotide. In general, column equilibration conditions may range from but are not limited to conductivity values of less than 0.1 mS/cm to more than 30 mS/cm, and pH values from less than 4.0 to greater than 9.0.

In certain embodiments where it is an objective of the technique to reduce contaminant levels, it will be advantageous to employ the lowest pH and/or the lowest conductivity that does not cause the polynucleotide to bind substantially to the negatively charged particles. It will be understood that the guidelines of lowest pH and/or lowest conductivity may be moderated according to the solubility and stability requirements of the antibody.

In certain embodiments, where the electronegative particles bear additional chemical functionalities, it may be necessary or beneficial to employ raise pH values or include additives that modulate the interactivity of the polynucleotide with the surface of the particles in order to practice the method. The simplest such variant may be to add NaCl or other salts. The most effective level can be determined experimentally by evaluating different increments of NaCl concentration, such as 25 mM, 50 mM, 100 mM, 200 mM etc. Once the effective range is determined, it may be refined with subsequent experiments conducted at finer increments or by means of statistical methods such as so-called Design of Experiments (DoE). Alternative salts may also be considered, as well as other additives including sugars, chaotropes, organic solvents, and surfactants, among others. Combinations of additives may also be evaluated, including in combination with various pH values.

In certain embodiments, the negatively charged particles residing within the column may be of a single type or of multiple types, including combinations of porous and nonporous particles, or combinations of porous particles with different pore sizes. Where the invention employs a combination of particles with pores of different sizes, one subset of particles may have pores of a size that physically excludes antibody, while another subset may have a pore size that does not exclude polynucleotide. In such a case, the subset with pores large enough to not exclude polynucleotide may present the ligand in such a way as to physically hinder pore entry by polynucleotide lacking a strong positive charge.

In certain embodiments, the invention may be used for the initial fractionation of polynucleotide from crude samples, or at any stage of purification; in any case illustrating that the invention may be combined with other purification methods to achieve the overall degree of purification required for a particular polynucleotide application.

In certain embodiments, the sample to be introduced may be concentrated by ultrafiltration.

In certain embodiments, it may be advantageous to expose the sample to a negatively charged surface or surfaces prior to its introduction to the column. Such exposure will be understood to remove highly electropositive sample components that might tend to foul the column used to practice the invention, but will also be understood to likely require development of special conditions to remove the fouling agents without loss of the polynucleotide. For example it may be necessary to add salt sufficient to prevent binding of the polynucleotide but not sufficient to prevent the binding of polynucleotide compaction proteins from the host cells in which the polynucleotide was produced. The negatively charged surfaces to which the sample may be exposed prior to practicing the invention may include particles, membranes, fibers, monoliths, or compound constructions.

In some embodiments, electronegative chromatography media employed in the void exclusion chromatography mode comprises one selected from the group consisting of cation exchangers, metal affinity media, and multimodal chromatography media, specific examples of which include Unosphere S and UNOsphere Rapid S; UNOsphere Profinity; Capto MMC, and other electronegative particle based media suitable for practicing the method. In some embodiments, any cation exchange media having electronegative groups may serve, however, those skilled in the art will that not all electronegative media are suitable. While the exact parameters that define a successful medium have not been fully elucidated, those skilled in the art can readily screen any particular electronegative media for its ability to perform in void exclusion anion exchange chromatography. At the most basic level, this is easily accomplished in a simple experiment where candidate cation exchange particles are packed in a column, for example with a volume of 20 mL. The particles are ideally allowed to settle by gravity, then a flow adaptor is set so that it contacts but does not significantly compress the bed. The technique may be performed on columns in which the bed has been compressed, but compression reduces the interparticle space with the direct result of reducing the volumetric sample capacity of the column. For example, a 20 mL gravity-settled bed may have a sample volume capacity as high as about 8 mL, but 25% compression of the bed to a volume of 15 mL, will reduce the capacity to a level lower than the capacity of 15 mL of the same media in a gravity-settled bed. This suggests, and experimental evidence tends to support the notion, that compression disproportionately reduces the interparticle volume, as opposed to the particle volume. The chromatography system on which the column resides is ideally configured in a way to deliver sample in a manner that does not cause significant dilution of the sample on the way to the column, since the technique depends on the volume of the sample entering the column being no greater than the interparticle volume of the column. Laminar flow is well known to dilute sample at the boundaries. In the example of a 5 mL sample loop with a length of a few meters, the volume of sample as it enters the column may be substantially greater than the 5 mL initially introduced into the loop, for example possible increasing to 7.5 mL or even 10 mL or more. Systems with a so-called superloop are well suited for practicing the invention, since by means of their reliance on a cylinder-plunger design they permit the application of large sample volumes without the imposition of excessive dilution through laminar flow. It will be understood by persons of ordinary skill in the art that any given chromatography system also imposes a certain amount of sample dilution between the sample-introducing device (injector) and the column as a result of fluid passing through various valves and mixers, and that as a general matter, the larger the ratio of the column volume to a particular system's internal pre-column dilution volume, the lower the relative increase in at-the-column sample volume as a function system dilution. In practical terms, this means that operating a small column on a chromatograph designed and configured for large scale use will impose serious secondary restrictions on the volume of sample that can be applied at the injector, while operating a large column on such a system will permit the user to apply samples of greater volume that remain within the volumetric limits of a given column at the point where the sample enters the column. With the 20 mL gravity packed uncompressed column on a system such as an AKTA Explorer 100 using the dark green peek tubing, and equipped with a superloop that has been previously loaded with sample containing a polynucleotide, and with the column equilibrated with 50 mM acetate, pH 4.0, a 1 mL sample is loaded to the column. A chart mark is made at the point where the antibody the antibody begins to exit from the column. Another chart mark is made at the point where the conductivity changes, indicating the passage of small molecules associated with the sample. The volume between the marks provides a serviceable estimate of the interparticle volume of the column. The ratio of the interparticle volume to the total column volume is calculated. Cation exchange chromatography media suited for performing the technique of void exclusion cation exchange chromatography will exhibit a ratio of about 1/2.5, but media exhibiting lower ratios, such as 1/2.4, 1/2.3, 1/2.2, 1/2.1, 1/2.0, or lower can provide useful results so long as the volume of the sample entering the column does not exceed the adjusted volume adjusted according to the above results. It is to be understood that the conditions suggested herein for determining the suitability of a given anion exchange medium for conducting void exclusion cation exchange chromatography with a polynucleotide are not necessarily the conditions to achieve the most effective contaminant removal, nor necessarily the conditions most suitable to all forms of polynucleotides. It is to be further understood that electronegative media that include additional chemical functionalities that cause them to be marketed for so-called multimodal chromatography will require an additional dimension of process development involving evaluation of different buffer conditions to determine if that given medium is suitable for performing adsorption chromatography in void exclusion mode. One example includes the so called mixed-mode or multimodal electronegative chromatography medium marketed under the commercial name of Capto MMC, which is purported to incorporate functional groups that cause it to participate in hydrogen bonds and hydrophobic interactions.

Additional objects and advantages of the invention will be set forth in part in the description which follows, and in part will be obvious from the description, or may be learned by practicing the invention. The objects and advantages of the invention will be realized and attained by means of the elements and combinations specified in the claims.

It is to be understood that both the foregoing general description and the following detailed description are exemplary and explanatory only and are not restrictive of the invention as claimed.

In preparation for using certain embodiments of the invention, the usable sample volume with respect to the column must be determined. In its simplest mode, where all of the particles in the column are negatively charged porous particles, this value may be estimated by multiplying the total volume of an uncompressed gravity-settled packed chromatography bed by 0.4. Permissible maximum sample volume may be determined precisely by a simple experiment in which the column is equilibrated to a low salt buffer at a moderate pH, and a sample of polynucleotide in a high salt buffer is applied, then followed with additional equilibration buffer. Mark the point at which polynucleotide begins to elute, as indicated by an increase in UV absorbance at 280 nm. Mark the point at which the high salt begins to elute, as indicated by an increase in conductivity. The volume between the marks represents the maximum sample volume per cycle for that column.

Suitable sample volumes for the performance of certain embodiments of the invention for columns that include additional particles other than porous electronegative particles (such as those bearing secondary chemical surfaces) can be estimated by multiplying the volume of only the negatively charged porous particles. The above experiment can be applied to specifically define the maximum sample. It will be apparent that the maximum sample volume for a given column of mixed negative and other particles will be reduced from exclusively negatively porous particle columns in proportion to the relative column volume occupied by the non-negative particles.

In certain embodiments, development of a method for purification of a particular polynucleotide preparation will generally begin with evaluation of the simplest option, which will be a column packed exclusively with negatively charged porous particles. Appropriate particles may consist of commercial chromatography media marketed for practicing the technique of so-called anion exchange chromatography. Examples of the dozens of such products include Capto S, Capto CM, Capto MMC, S Sephadex, CM Sephadex (GE Healthcare); GigaCap S and S-Toyopearl (Tosoh Bioseparations); Macroprep High-S, UNOsphere S, UNOsphere Rapid S, Nuvia S, Profinity (Bio-Rad Laboratories); Eshmuno S, S Fractogel, (Merck); and S-HyperD (Pall). Such products are not at present labeled with respect to the identity or concentration of secondary functionalities on their surfaces, nor the pore size, nor exclusion limit, nor virtual pore size resulting from their respective employment of ligand grafting methods to enhance their functionality, nor is such information generally available from suppliers. It should be anticipated that all such products include multiple physical and chemical functionalities, and that it will be prudent to evaluate more than one product to determine which is inherently most suitable for purification of a particular polynucleotide preparation. In one embodiment, evaluation may begin with UNOsphere S and UNOsphere Rapid S, Capto MMC or a smaller subset of candidates.

For any given polynucleotide, it will be advisable to evaluate a range of pH and conductivity values to which the column is initially equilibrated. As a general matter, contaminant reduction is best at the lowest pH and lowest conductivity at which the polynucleotide remains soluble and stable, so initial conditions of a moderately acidic buffer such as 20-50 mM acetate, pH 4.5, may be a convenient place to start. Lower and higher pH values may be subsequently evaluated, with pH values as low as 2.0 or higher than 9.0, and conductivity values ranging from less than 0.1 to more than 30 mS/cm.

It may be useful in some embodiments to evaluate conditions that render the eluted sample suitable for application to a subsequent purification step without requirement for further sample preparation. For example, if the eluted sample is to be applied subsequently to an anion exchange column at a pH of 6.0, it may be desirable to equilibrate the column to a pH 6.0. If the eluted sample is to be applied subsequently to a hydroxyapatite column, it may be suitable to employ neutral pH and set the phosphate concentration of the buffer at the level required by the hydroxyapatite column, and to omit chelating agents such as EDTA or citrate. In any case where the equilibration buffer is selected for continuity with a subsequent fractionation method, low pH low conductivity conditions will still be generally evaluated to ensure that purification potential is not sacrificed in the present step.

Without being bound to any particular theory, it is believed that the method is virtually independent of sample composition. Consequently, in certain embodiments, the sample may contain a variety of agents, individually or in combination, to enhance dissociation polynucleotide-contaminant complexes.

In certain embodiments where the polynucleotide in the sample has been treated previously with dissociating agents as described above; or if the method is to be practiced on samples of unpurified cell culture supernatant, the performance of the method may be enhanced by using negatively charged porous particles that embody substantial secondary functionalities. Examples may include porous particle-based commercial chromatography products that embody positive charges deliberately combined with secondary functionalities. Such media are commonly referred to as mixed modes. Capto MMC (GE healthcare) and Nuvia cPrime (Bio-Rad Laboratories) are examples of commercial mixed mode chromatography products combining positive charges with functionalities that confer the ability to participate in hydrophobic interactions, pi-pi bonding, and hydrogen bonding. Similar combinations are known in the literature and additional commercial entries can be expected. It will be apparent to the skilled person in the art that the formulation of the equilibration buffer may need to be modified to prevent retention or retardation by the secondary functionalities. In the case of Capto MMC Nuvia cPrime, for example, it may be necessary to operate at a higher pH and higher conductivity than would be required with chromatography media marketed for cation exchange. Another class of so-called multimodal negatively charged media may include so called immobilized metal affinity chromatography ligands (IMAC) such as iminodiacetic acid or nitriloacetic acid. Inclusion of secondary functionalities does not however impair the ability of the invention to accommodate samples without respect to sample composition. This is a fundamental and important distinction from standard flow-through and bind-elute methods which are wholly unable to achieve fractionation in the presence of samples with high conductivities.

In certain embodiments where the sample includes compositions such as described above, it may alternatively be useful to combine porous electronegative particles with distinct particles that embody secondary chemical functionalities, and pack the two or several particle types together in the same column. Particles bearing secondary functionalities may be porous or non-porous. As above, the method remains independent of sample composition. Likewise, equilibration conditions may be limited by the need to suspend interactions between the antibody and the secondary functionalities. For example, if particles bearing a positive charge functionality are present and a particular polynucleotide has a strong tendency to bind such charges, it may be necessary to decrease pH and/or increase conductivity. The favorable trade-off in this case as above, is that the inclusion of one or more secondary functionalities may enable a higher degree of purification.

In certain embodiments where porous electronegative particles are combined with distinct particles that embody secondary functionalities, the latter may be layered on top of the bed of electronegative particles or packed in a separate column that may be plumbed immediately before or immediately after the column of electronegative particles. In some embodiments, the porous electronegative particles are mixed with separate particles bearing secondary functionalities.

In certain alternate embodiments, the method may be practiced such that the secondary particles may be added directly to the sample in advance to scavenge the potentially troublesome contaminants and the particles are then separated from the sample such that the partially purified sample is then contacted with the column.

When developing particle mixtures to optimize purification of a particular polynucleotide, the secondary functionalities may be selected alternatively or in addition according to their ability to enhance pH control and/or reduce buffer volumes required to titrate the column to its desired operating pH. For example, anion exchangers are known to produce uncontrolled temporary pH increases when exposed to elevated conductivity. They produce uncontrolled temporary pH reductions when conductivity is reduced. The magnitudes and durations of these effects vary with the conductivity differential between steps, the charge characteristics of the exchanger, and buffer capacity. Cation exchangers suffer the same problem but the direction of the uncontrolled pH excursions is opposite to those that occur with anion exchangers. Combining a secondary electropositive functionality with a primary electronegative functionality thus reduces the magnitude and duration of pH excursions. The ideal mix of functionalities may be readily determined by experimentation.

In certain embodiments employing additional particles with functionalities distinct from the electronegative particles, and where those distinct particles are mixed with or packed in a column preceding the electronegative particles, it may be necessary to adjust the initial sample volume down from the amount that would be applied to a column of exclusively electronegative particles to account for the increase in sample volume that occurs as a result of dispersion of the polynucleotide as it diffuses during its passage through the column. The necessary degree of reduction of initial sample volume, if any, may be easily determined by simple experimentation, where the criterion is the elution of the polynucleotide within the equilibration buffer.

In certain embodiments, the method is distinguished from other applications of negatively charged porous particles due to its effectiveness being independent of the composition of the buffer applied immediately after sample application. In many instances, it will be advantageous to follow the sample application immediately with a buffer composition intended to completely elute materials bound to the porous particles. For example, a column may be equilibrated to 25 mM acetate, pH 4.5. polynucleotide-containing cell culture supernatant containing 1.0 M sodium chloride, pH 7.0, is applied in a volume amounting to 35% of the column volume, then followed with 2 M sodium chloride, pH 8.0. The substantially purified polynucleotide elutes in the acetate buffer. This occurs because the polynucleotide travels exclusively through the inter-particle space, as described above, while chase-buffer must also travel through the intra-particle pore space. The compelling feature of this approach is that it supports the unique ability to elute contaminants and clean the column simultaneously, with the practical benefit of shortening the process cycle, reducing process time and material usage. This makes it attractive to perform multiple cycles on a small column rather than a single cycle on a large column, which further reduces material usage.

In certain embodiments, it may be advantageous to follow the sample with equilibration buffer, or a buffer of lower conductivity, for example 20 mM acetate, pH 4.0, for the express purpose of enhancing retention of acidic contaminants with a hydrodynamic size greater than the average pore diameter of the electronegative porous particles, such as polynucleotide, since they may otherwise elute at the trailing boundary of the polynucleotide and potentially contaminate it to an excessive and unnecessary degree. To the extent that the column may include an increment of electropositive particles, this may also enhance removal of electronegative contaminants. The ideal volume of low-conductivity chase-buffer may be determined experimentally, beginning with about 50% of the packed column volume.

In certain embodiments, the method supports faster flow rates than are generally used for chromatography on porous particles. This is because the polynucleotide travels exclusively through the inter-particle space where mass transport is convective, and is therefore not affected by the slow diffusion constant of the polynucleotide, nor by flow rate or sample viscosity. Thus the method can be practiced with high efficiency at linear flow rates up to 1000 cm/hr or more, versus usual porous particle chromatography operations that are carried out at 50-100 cm/hr or less. Flow rates above 300 cm/hr however may require a reduced sample volume. This is because mass transport for contaminants able to enter pores is diffusive, becoming less efficient with increasing flow rate or sample viscosity. Excessive flow rates afford less opportunity for contaminants to achieve diffusive equilibrium with the pores of the porous particles. Experimentation will reveal the ideal flow rate for any given polynucleotide and set of buffer compositions.

In certain embodiments where the electronegative porous particles are combined in a column of porous particles bearing other surface chemistries, it will generally be useful to base the maximum sample volume on the volume of the electronegative particles only. Even then, it may be prudent to determine maximum sample volume experimentally since the presence of particles lacking an electronegative surface may have the effect of diluting the sample within the column.

In certain embodiments, particles bearing surface chemistries other than electronegativity may be packed in a separate column that is plumbed in series with the column of electronegative particles. In such a configuration, the same cautions may be applied as those discussed for the situation where other-chemistry particles are mixed in the same column with electronegative particles.

In certain embodiments, methods disclosed herein may be used for the initial purification step following sample preparation. In other embodiments, it may be used for intermediate purification, or it may be used for final purification. It will be apparent to those skilled in the art that in any case where the method is not used as the last step in a process, it has the ability to facilitate overall process continuity by virtue of its ability to buffer exchange the sample coincident with reduction of contaminants.

In certain embodiments, the invention may be practiced in conjunction with other purification methods. Specifically, it may be used in any combination with size exclusion, anion exchange, cation exchange, hydrophobic interaction, preferential exclusion, hydroxyapatite or other forms or mixed mode chromatography, or bioaffinity chromatography; also in conjunction with precipitation, crystallization, ultracentrifugation, and methods of aqueous two-phase partitioning.

After obtaining the processed polynucleotide, the contents of the column may be discarded. Alternatively, the column may be cleaned with high concentrations of salt then restored to original conditions by re-equilibration so that it may be used for additional cycles. The column may also be sanitized with appropriate agents such as sodium hydroxide.

In certain embodiments, the invention may be mechanized and automated to increase throughput. In certain such embodiments, for example, the method may include an automated multicolumn system such as used to perform simulated moving bed chromatography.

EXAMPLES

The following Examples are provided for guidance in the practice of the invention. While the Examples provided show various purifications of DNA in particular, those skilled in the art will appreciate that similar conditions and principles may apply to the purification of RNA and other natural or unnatural polynucleotides. Moreover, one skilled in the art will appreciate that appropriate precautions may be necessary to operate with some nucleotides, such as RNA due to their greater instability. Such necessary precautions are well within the purview of those skilled in the art.

Example 1

A column was packed with a porous particle cation exchange medium (Nuvia S, Bio-Rad). The column was equilibrated with 50 mM Hepes, pH 7.0. Mammalian (Chinese Hamster Ovary (CHO)) cells were homogenized in 4 M guanidine. Physical debris was sedimented by centrifugation. Supernatant in 4 M guanidine amounting to 20% of the column volume was applied to the column, and the sample was chased with equilibration buffer. More than 90% of the DNA eluted in the equilibration buffer. Proteins and other contaminants were removed later, in conjunction with the passage of the guanidine from the original sample.

Example 2

Purified DNA from salmon sperm was applied to a column as described in Example 1. The equilibration buffer was 50 mM Tris, pH 8.0, which resulted in the DNA eluting in that buffer. The eluted DNA was applied directly to an anion exchange monolith (QA) equilibrated to the same conditions. The DNA was subsequently eluted from the anion exchange monolith with a salt gradient, eluting at a conductivity of about 60 mS/cm. This example illustrates how the invention may be used to purify DNA and prepare the sample for a subsequent process step in a single unit-operation.

Example 3

Purified DNA from salmon sperm was applied to a Nuvia S column as described in Example 2. The equilibration buffer was 50 mM Hepes, 50 mM phosphate, pH 7.0, which resulted in the DNA eluting in that buffer. The eluted DNA was applied directly to column of hydroxyapatite (CHT type I, 40 micron), then eluted in a phosphate gradient, eluting over a range of phosphate concentrations of about 225 to 275 mM phosphate mS/cm. This example provides another illustration of how the invention may be used to purify DNA and prepare the sample for a subsequent process step in a single unit-operation. It will be apparent to persons of ordinary skill that the invention could be similarly used to link two purification steps, for example performing an initial purification step with hydroxyapatite, using the invention to achieve additional purification while equilibrating the sample for application to an anion exchange column, then performing the anion exchange step. It will be apparent to persons of ordinary skill that such 3-step processes may be suitable for the purification of gene therapy vectors to a level suitable for in vivo human therapy.

Example 4

Purification of DNA from fresh mammalian cells. Chinese hamster ovary cells from cell culture were concentrated by centrifugation. The supernatant was discarded, and dry guanidine added directly to the sample to create a final concentration of 3 M. The cells were manually homogenized in guanidine, then the particulates mostly removed by centrifugation, followed by their complete removal by filtration through a 0.45 micron membrane. A 5 mL sample of the clear supernatant was applied to a 20 mL column of UNOsphere Rapid S, equilibrated to 0.05 M acetate, pH 4.1. The sample was followed by sufficient buffer to impel the sample through the column. The column effluent was monitored simultaneously at 254 and 280 nm. The 254/280 ratio of the eluted peak was about 1.7 indicating highly but incompletely purified DNA. Contaminants and guanidine eluted in a second peak and were discarded. The DNA-containing sample in 0.04 M acetate pH 4.1 was titrated to pH 7.0 and applied to a QA 334 microliter monolithic disk equilibrated to the same conditions for further purification. The monolith was eluted with a 5 minute linear gradient to 1 M NaCl (4 mL/min). The DNA eluted in a sharp peak with a 254/280 ratio of 2:1 at 0.6 M NaCl, indicating a very high degree of purity.

Example 5

Purification of DNA from dried mammalian cells. The form of example 4 was followed, except that the CHO cells smeared in a thin layer on a petri dish were dried overnight in a fume hood, and then homogenized in 5 M guanidine, pH 5. Results were the same as obtained in Example 4.

Example 6

DNA purification on a negatively charged hydrophobic multimodal chromatography medium. Purified genomic DNA from salmon sperm was resuspended in 50 Hepes, 100 mM NaCl, pH 7.0. The sample was filtered through a 0.22 micron membrane to remove particulates, then 5 mL was applied to a 20 mL column packed with Capto MMC, a multimodal chromatography medium consisting of negative charges, hydrophobic residues, and hydrogen bonding residues, equilibrated to 50 mM acetate, 100 mM NaCl, pH 4.0. 90% of the DNA partitioned completely to the void volume and eluted in the acetate buffer, the remainder eluted in after the passage of salt through the column.

Example 7

DNA purification on a negatively charged metal affinity multimodal chromatography medium. Purified genomic DNA from salmon sperm was resuspended in 50 Hepes, 100 mM NaCl, pH 7.0. The sample was filtered through a 0.22 micron membrane to remove particulates, then 5 mL was applied to a 20 mL column packed with Capto MMC, a multimodal chromatography medium consisting of negative charges configured to impart metal affinity (UNOsphere Profinity), equilibrated to 50 mM acetate, 100 mM NaCl, pH 4.0. The DNA partitioned completely to the void volume and eluted in the acetate buffer.

Given the importance of sample volume relative to column volume, the person of skill in the art will recognize the importance of applying sample in a way that does not result in uncontrolled dispersion of the sample at the sample boundaries, which would have the effect of inadvertently increasing the volume of the sample before it can enter the column. Sample was applied in all of the above examples by means of a device called a superloop, that particularly avoids dispersion at the sample boundaries.

It will be apparent to the person of ordinary skill in the art that they sample may be applied for purification of other polynucleotides with equal expectation of success. Examples particularly include RNA.

The present invention may be combined with other purification methods to achieve higher levels of purification. Examples of such other purification methods include, but are not limited to, other methods commonly used for purification of polynucleotide such as ultracentrifugation, ultrafiltration, density gradient filtration, affinity chromatography, anion exchange chromatography, cation exchange chromatography, hydrophobic interaction chromatography, immobilized metal affinity chromatography, and additional mixed mode chromatography methods; also methods of precipitation, crystallization, and liquid-liquid extraction. It is within the purview of a person of ordinary skill in the art to develop appropriate conditions for the various methods and integrate them with the invention herein to achieve the necessary purification of a particular polynucleotide.

All references cited herein are incorporated by reference in their entirety and for all purposes to the same extent as if each individual publication or patent or patent application was specifically and individually indicated to be incorporated by reference in its entirety for all purposes. To the extent publications and patents or patent applications incorporated by reference contradict the disclosure contained in the specification, the specification is intended to supersede and/or take precedence over any such contradictory material.

All numbers expressing quantities of ingredients, chromatography conditions, and so forth used in the specification and claims are to be understood as being modified in all instances by the term "about." Accordingly, unless indicated to the contrary, the numerical parameters set forth in the specification and attached claims are approximations that may vary depending upon the desired performance sought to be obtained by the present invention.

Many modifications and variations of this invention can be made without departing from its spirit and scope, as will be apparent to those skilled in the art. The specific embodiments described herein are offered by way of example only and are not meant to be limiting in any way. It is intended that the specification and examples be considered as exemplary only, with the true scope and spirit of the invention being indicated by the following claims.

The invention claimed is:

1. A method of purifying a polynucleotide by void exclusion chromatography from a sample comprising a polynucleotide, the method comprising the steps of (i) providing a packed chromatographic column comprising negatively charged porous particles, wherein the negatively charged porous particles comprise cation exchange particles having an exposed negatively charged surface conferred by one or more negatively charged moieties (ii) equilibrating the packed chromatographic column to conditions that allow the polynucleotide to elute, wherein the conditions comprise a pH in a range from 2 to 10 and a conductivity in a range from 0.1 mS/cm to 30 mS/cm, (iii) contacting the sample comprising the polynucleotide with the negatively charged porous particles of the packed chromatographic column, wherein the sample is contacted with the exposed negatively charged surface of the particles, and a volume of the sample applied consists of a volume that is less than or equal to the void volume of the negatively charged porous particles within the packed chromatographic column, and (iv) collecting a column effluent from the packed chromatographic column, wherein the column effluent comprises the polynucleotide and the column effluent is in the same conditions to which the column was equilibrated.

2. The method of claim 1, wherein the polynucleotide is genomic DNA, mitochondrial DNA, chloroplast DNA, plasmid DNA, single stranded DNA, or double stranded DNA.

3. The method of claim 1, wherein the sample may be unpurified, at an intermediate level of purity, or highly purified.

4. The method of claim 1, wherein the polynucleotide has been concentrated prior to its application to the column.

5. The method of claim 1, wherein the polynucleotide has been concentrated by ultrafiltration prior to its application to the packed chromatographic column.

6. The method of claim 1, wherein, prior to (iii), the sample is exposed to a second negatively charged surface or surfaces comprising one or more second particles, a membrane, fibers, or a monolith at conditions of pH, salt concentration, or conductivity that provide a substantial absence of binding of the polynucleotide to the second negatively charged surface or surfaces.

7. The method of claim 6, wherein the second negatively charged surface or surfaces further comprise secondary reactivities comprising the ability to participate in hydrophobic interactions, metal affinity interaction, or combinations thereof.

8. The method of claim 6, wherein the second negatively charged surface or surfaces comprise a membrane, a monolith, a fiber, plurality of fibers, a particle, or plurality of particles.

9. The method of claim 1, wherein the packed chromatographic column is packed solely with negatively charged porous particles and a sample volume is less than 40% of the volume of the packed chromatographic column.

10. The method of claim 1, wherein the packed chromatographic column is equilibrated to a pH in a range of from about 2 to about 9.

11. The method of claim 1, wherein the packed chromatographic column is equilibrated with a buffer having a pH in a range selected from the group consisting of (1) from about 2 to about 8, (2) from about 4 to about 7, and (3) from about 4.5 to about 6.0.

12. The method of claim 1, wherein the packed chromatographic column is equilibrated to a conductivity value in a range of from about 0.1 mS/cm to about 15 mS/cm.

13. The method of claim 1, wherein the packed chromatographic column is equilibrated to conditions at or close to a sample application condition for use in a subsequent purification step to be performed upon an eluate comprising the polynucleotide.

14. The method of claim 1, wherein a sample application condition for contacting the sample with the packed chromatographic column comprises a pH in range of from about 2 to about 10.

15. The method of claim 1, wherein a conductivity value of the sample for contacting the sample with the packed chromatographic column comprises a range of from a non-zero conductivity up to a conductivity corresponding to a saturated solution of a particular salt or combination of salts.

16. The method of claim 1, wherein the step of equilibrating the packed chromatographic column comprises applying to the packed chromatographic column an equilibration buffer having a pH in a range of about 4 to about 9.

17. The method of claim 16, wherein a conductivity value of the equilibration buffer comprises a range of from about 0.1 mS/cm to about 30 mS/cm.

18. The method of claim 1, wherein the electronegativity is conferred to the negatively charged porous particles by a moiety selected from the group consisting of a carboxyl, a sulfo, or a phosphor moiety.

19. The method of claim 1, wherein the packed chromatographic column comprises one or more second particles in addition to the negatively charged porous particles, wherein the one or more second particles possess one or more secondary chemical functionalities selected from the group consisting of anion exchange, hydrophobic interactions, hydrogen bonding, pi-pi interactions, and metal chelation.

20. The method of claim 1, wherein at least one of the negatively charged porous particles possess one or more secondary chemical functionalities selected from the group consisting of anion exchange, hydrophobic interactions, hydrogen bonding, pi-pi interactions, and metal chelation.

21. The method of claim 1, further comprising the additional step of contacting the sample with one or more contaminant-dissociating agents prior to the step of contacting the sample with the packed chromatographic column.

22. The method of claim 21, wherein the contaminant-dissociating agent is selected from the group consisting of salts, nonionic organic polymers, organic solvents, surfactants, and chaotropes, prior to the step of contacting the sample with the column.

23. The method of claim 22, wherein the contaminant-dissociating agent is a nonionic organic polymer selected from the group consisting of polyethylene glycol, polypropylene glycol and polybutylene glycol.

24. The method of claim 23, wherein the nonionic organic polymer has an average molecular weight is in a range of from about 130 D to about 1000 D.

25. The method of claim 22, wherein the contaminant-dissociating agent is an organic solvent selected from the group consisting of ethylene glycol, propylene glycol, butylene glycol, dimethylsulfoxide, ethanol, and phenoxyethanol.

26. The method of claim 22, wherein the contaminant-dissociating agent is provided at a concentration in a range of from about 0.01% to about 25% weight/volume.

27. The method of claim 22, wherein the contaminant-dissociating is a surfactant selected from the group consisting of Tween, triton, CHAPS, CHAPSO and octyl glucoside.

28. The method of claim 27, wherein the surfactant is provided at a concentration in a range of from about 0.001% to about 1% weight/volume.

29. The method of claim 28, wherein the surfactant is provided at a concentration in a range of from about 0.001% to about 0.1% weight/volume.

* * * * *